United States Patent [19]

Bartolucci

[11] Patent Number: 4,929,446
[45] Date of Patent: May 29, 1990

[54] UNIT DOSAGE FORM
[75] Inventor: Raymond A. Bartolucci, New City, N.Y.
[73] Assignee: American Cyanamid Company, Stamford, Conn.
[21] Appl. No.: 183,683
[22] Filed: Apr. 19, 1988
[51] Int. Cl.⁵ .......................................... A61K 47/00
[52] U.S. Cl. .................................................. 424/439
[58] Field of Search ......................... 424/439, 440, 441
[56] References Cited
U.S. PATENT DOCUMENTS 2,580,683  1/1952  Kreuger ............................. 424/455
4,260,596  4/1981  Mackles ............................. 424/440
4,752,485  6/1988  Sharma et al. ....................... 426/99
4,753,790  6/1988  Silva et al. ......................... 424/440

Primary Examiner—Ellis P. Robinson
Assistant Examiner—P. L. Prater
Attorney, Agent, or Firm—H. G. Jackson

[57] ABSTRACT

The present invention discloses edible unit dosage form for delivering a medicament comprising a relatively hard, unitary outer shell composed essentially of sugar which emcompasses a liquid or semi-solid center core containing the medicament dose accurate to within about ±5% of the prescribed dosage, and a method for production of said unit dosage form.

16 Claims, 2 Drawing Sheets

UNIT DOSAGE FORM

FIELD OF THE INVENTION

The present invention relates to a unit dosage form for delivering a specific dose of a liquid or semi-solid medicament and the process for manufacture thereof. More specifically, a unit dosage form has been found which comprises an edible relatively hard unitary outer shell which serves to contain the liquid or semi-solid center and enables the product to be handled and chewed or dissolved to deliver the specific medicament dose.

BACKGROUND OF THE INVENTION

Use of a hollow shell to contain a liquid center is well known in the art. The teachings of Liebich, U.S. Pat. No. 943,945, dated Dec. 21, 1909, discloses a hollow or empty body preferably made of sugar, enveloped or encased in an edible substance such as biscuit, chocolate, cake or sugar, which contained a liquor therein.

Similarly, Silver, U.S. Pat. No. 2,531,536, dated Nov. 28, 1950, teaches a liquid containing product but is more specifically concerned with a "flavor-bud" comprising a hard shell made of, among other things, a sizable quantity of anhydrous dextrose and some glucose, and a viscous liquid flavored center.

Kreuger et al., U.S. Pat. No. 2,580,683, dated Jan. 1, 1952, describes a capsule, capable of being filled with an aqueous solution, containing sugar in the gelatin employed to form the capsule.

In describing a unit dosage form of liquid or gel, Mackles, U.S. Pat. No. 4,260,596, dated Apr. 7, 1981, discloses a hard shell formed of two pieces, a cavity and a top, joined with a sealing material, encompassing a liquid or gel center, said shell utilizing mannitol rather than sugar as the shell forming ingredient.

Although there have been suggestions in the prior art of forming liquid center products encompassed to a shell comprising sugar, this procedure has found little favor in practice. Heretofore, molding of a sugar-comprised shell has demonstrated problems in crystallization during cooling, and stability and integrity due to moisture. Mackles, in particular, states that sugar is entirely unsuitable because molten sugar does not crystallize quickly on cooling, and cools to a tacky, amorphous state which sticks to the mold.

Furthermore, accurate dosages of the liquid or semi-solid center could not be achieved because of inaccurate methods of forming the shell and adding the liquid or semi-solid center.

It is therefore a primary object of the present invention to provide an edible unit dosage form which is capable of delivering an accurate dose of a liquid or semi-solid medicament.

It is a further object of this invention to encompass the liquid or semi-solid medicament in a relatively hard, unitary shell comprising sugar.

It is yet another object of this invention to provide a process for the manufacture of an edible unit dose form of an accurate amount of a liquid or semi-solid medicament encompassed in a relatively hard shell comprising sugar, specifically sucrose and/or glucose.

SUMMARY OF THE INVENTION

The foregoing objects and other objects inherent from the following disclosure are accomplished by the present invention and the process for the production thereof.

The invention in its broadest aspect comprises an edible unit dosage form for delivering a medicament comprising a relatively hard unitary outer shell which is essentially comprised of a sugar which crystallizes slowly from the melt, said sugar comprising sucrose, glucose or mixtures thereof, and a liquid or semi-solid center contained within the shell comprising a dose of a medicament accurate to within about ±5% of a prescribed dosage.

The outer shell described herein is essentially composed of sugar taken from the group of sugars comprising essentially sucrose, glucose and mixtures thereof. Other ingredients in the shell optionally include flavorings and/or therapeutic amounts of medicaments such as menthol-eucalyptus, benzocaine and mixtures thereof.

The liquid or semi-solid center may include a sugar syrup, along with the medicament dose, for flavor. An example of the medicament may be a cough suppressant, antibiotic or other medicine in liquid or semi-solid form. Accuracy of dosage achieved permits use of the present invention with prescription drugs.

The process for production of the edible unit dosage form of the present invention comprises the simultaneous addition of the composition comprising the outer shell and the composition comprising the liquid or semi-solid center in side by side injector alignment, into a mold wherein the liquid or semi-solid center has a moisture content equal to or below that of the shell composition and is accurately dosed to within ±5% of the prescribed dosage. Accurate measurement of the liquid or semi-solid medicament is provided by adjustment of the feeder which injects the components of the unit dosage form into the mold. Moisture content of the liquid or semi-solid center composition is reduced by heat and vacuum until it is equal to or below that of the outer shell composition. Regulation of the component moisture contents allows simultaneous injection of the components into a mold without an intermixing of the components. A unitary outer shell is produced by the simultaneous addition of the shell composition and the center composition.

DETAILED DESCRIPTION OF THE INVENTION

Figure 1:
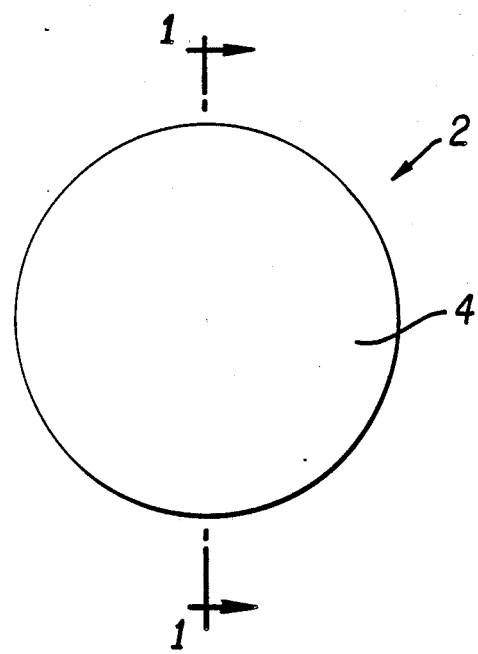
FIG. 1 is an elevational view of the unit dosage form of the present invention.
Figure 1A:
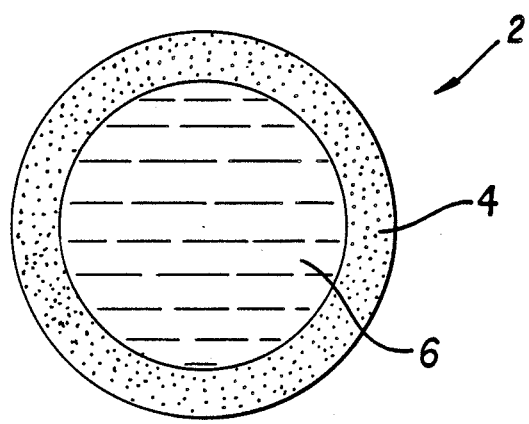
FIG. 1A is a cross-sectional view of the unit dosage form through line 1—1 of FIG. 1.

As best seen in FIGS. 1 and 1A, a unit dosage form 2 of the present invention comprises a relatively hard outer shell 4 comprising essentially a sugar which crystallizes slowly from the melt, said sugar comprising sucrose, glucose or mixtures thereof and a liquid or semi-solid center 6 comprising a medicament in a therapeutic amount accurate to within ±5% of the prescribed dosage, making it suitable for dispensing prescription drugs. The product of the present invention comprises a form of taking medication which is easy to handle and convenient to take. A sugar syrup may be included in the liquid or semi-solid center composition 10 for improved flavor, which provides a pleasant taste.

Figure 2:
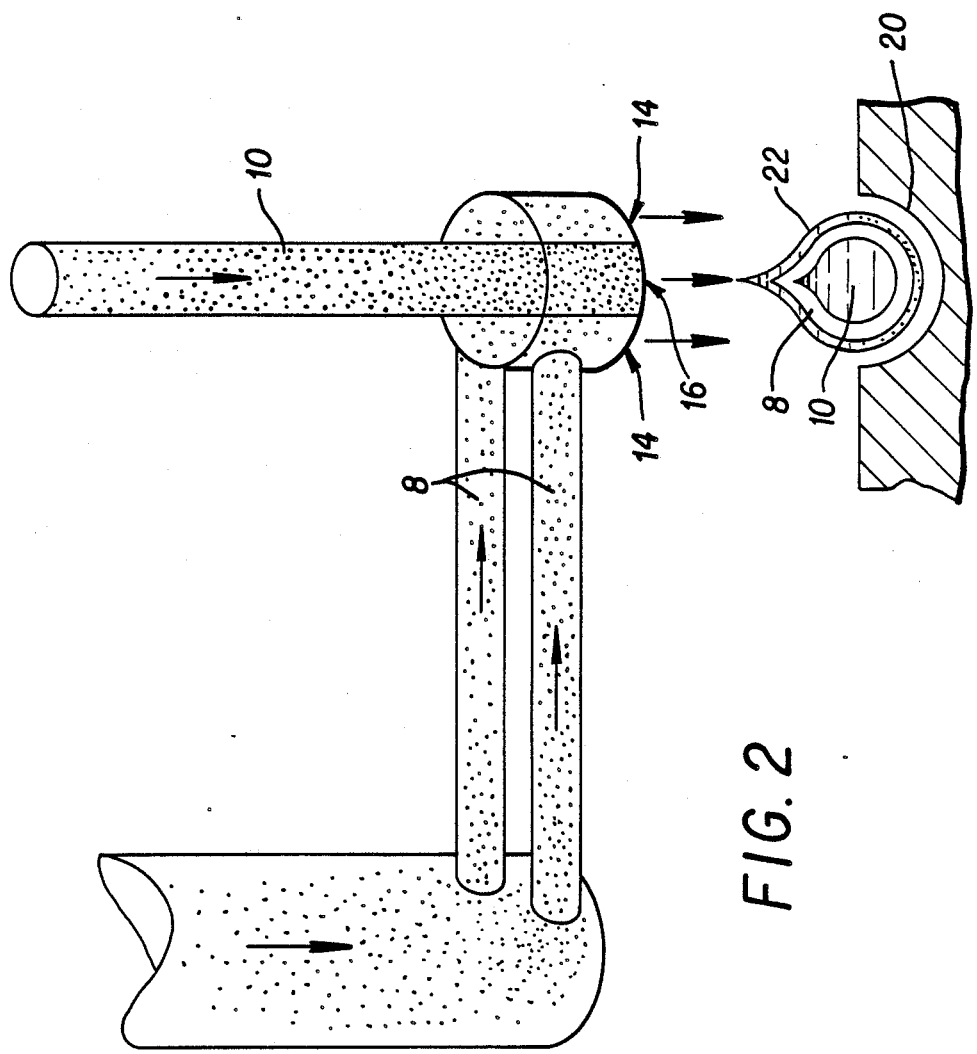
FIG. 2 is a plan view of the composition feeds of the molding machine used in the production of the present invention.

The outer molten shell composition 8 is essentially comprised of a sugar which crystallizes slowly, said sugar comprising sucrose, glucose, or mixtures thereof and optionally flavorings and therapeutic medicaments such as the anesthetic benzocaine. In one manner of proceeding, the glucose, sucrose and water are placed in an autofeed weigher of a suitable apparatus. A preferred apparatus is the Baker Perkins Candymolder ® which is microprocessor controlled. This is described in the literature, especially in a May, 1985 publication by Baker Perkins BCS Limited, entitled Quality Candy Production, 16 pages. Further details of center-filled candymaker apparatus are given in U.K. Patent Application No. 2018668A, Oct. 24, 1979. As shown in FIG. 2, measured amounts are heated, at which time the optional benzocaine and flavors are added, heating continuing. This molten shell composition 8 is transferred to a microfilm buffer tank where agitation is maintained. The shell composition 8 is then pumped into a microfilm cooker where it flows into the "shell hoppers", which feed the shell injectors 14, by the use of a rotating cone. Flavor pumps can then be activated to provide flavor to the molten shell composition 8.

The center composition 10 is prepared from the addition of a homogeneous medicament mix to a cooked sugar syrup mix in a vacuum cooker. Under heat and vacuum the moisture content of the center composition 10 is reduced to or below that of the molten shell composition 8. The moisture content of the center composition 10 should be about 5% $H_2O$ and is preferably about or less than 3% $H_2O$. The center composition 10 is then removed from the vacuum cooker to a jacketed conditioning kettle where such optional ingredients as menthol and/or flavorings can be added. The center composition 10 in this form is added to the molding machine in the "center hopper" which feeds the center injector 16.

The heated molten shell composition 8 and center composition 10 are then fed through the cylinders to the injectors and into a waste tray to be sure the system is full.

A sample is run to weight the components and make any necessary flow adjustments. Fine tuning of the equipment allows doses of the composition to achieve accuracy to within about ±5% of the prescribed dosage.

The separate compositions 8 and 10 are then deposited into a mold 20 simultaneously, the shell injectors 14 being placed laterally to the center injector 16 (See FIG. 2). The molten shell composition 8 forms in the mold around the center composition 10 in a unitary structure, encompassing the center composition 8. The molten unit dosage form 22 in the mold 20 is allowed to solidify and harden, whereafter it is released from the mold 20 in the finished unit dosage form 2.

DETAILED DESCRIPTION OF THE PREFERRED EMBODIMENT

The product and process described hereunder illustrate the preferred embodiment and are not intended to limit the invention in any way.

An edible cough and cold product in the unit dosage form of the present invention, comprising an edible, relatively hard, unitary outer shell which comprises essentially a sugar comprising sucrose and glucose, which crystallizes slowly from the melt, and a liquid or semi-solid medicament center wherein the medicament dose is provided within about ±5% by weight of the prescribed dosage is produced. The outer shell comprises, along with glucose and sucrose, menthol-eucalyptus and benzocaine. The unitary shell encompasses a liquid or semi-solid medicament center comprising dextromethorphan as the active therapeutic medicament and a sugar syrup for flavoring.

The following steps comprise the process for producing said product but are not intended to limit the product or process in any way:

STEP #1

Center Preparation

Premix #1

Weigh: 12.28 Kg Dextromethorphan Hydrobromide 10% Adsorbate and 21.46 Kg Glycerin.

Add to 80 qt Hobart Mixer approximately 10.0 Kg of glycerin, 12.28 Kg DMHB then another 11.46 Kg of glycerin and mix at speed #1 for 10 minutes.

Weigh: 9.47 Kg DMHB and 21.46 Kg glycerin.

To paste in Hobart, add 9.47 DMHB and 10.0 Kg of glycerin. Mix at speed #1 until smooth paste forms. Increase speed to #2 and mix for ten minutes. Add remaining 11.46 Kg of glycerin and mix at speed setting #1. Scrape sides to ensure complete homogenity of mix. Transfer mix into tared holding containers, label and record the yield.

Theoretical yield 64.67 Kg.

STEP #2

Premix #2

Sugar Components for Center

Add 38.70 Kg of sugar into the vacuum cooker. Add 47.30 Kg of Glucose Syrup 63DE into the vacuum cooker. Add 10.0 Kg of drinking water, and 50 gm of FD&C Red #40 into the vacuum cooker. Mix the components in the vacuum cooker and begin heating. Heat the syrup until 124° C. at 17 inches of vacuum.

STEP #3

Mixing Premix #1 and Premix #2

Add to the vacuum cooker containing the cooked syrup (Step #2) 64.67 Kg of Premix #1 (DMHB/Glycerin). Mix, and flush tank ball valve, continue to mix syrup for 10 minutes. After 10 minutes close vacuum tank cover and begin drawing a vacuum to 22 inches for three (3) minutes. Transfer syrup to jacketed conditioning kettle and maintain syrup temperature at 45°–55° C. At 45°–55° C. add 140 gm of 1-Menthol and 1160 gm of Cherry flavor Natural and Artificial. Mix syrup slowly for 15 minutes. This syrup is ready for depositing Step 5.

START-UP PROCEDURE FOR DEPOSITING

STEP #4

Set autofeed microprocessor of the Baker-Perkins Candymolder ® to weigh 27 Kg of water, 75 Kg glucose HM 43DE, and 75 Kg granulated white sugar. Press "on" for weighing process to begin. Tranfer slurry to J63 and begin heating until 108° C. At 108° C. add 7.5 gm of FD&C Red #40 and 413 gm of Benzocaine to J63. Continue heating syrup to 110° C. and transfer syrup to microfilm buffer tank. Maintain constant agitation in buffer tank. This syrup is ready for cooking in the microfilm cooker.

STEP #5

Activate power supply on microfilm control panel. Activate hopper heaters on the control panel. Set outer shell hopper temperature to 135° C. and set center shell hopper to 50° C. Meter, by pump, syrup from buffer tank to BP microfilm cooker. Cook the syrup to 145° C. at open vacuum. Discharge the syrup film from cooker and adjust the rate to 3.6 Kg/min.

Fill the "center" hopper with center syrup. Begin to deposit center syrup in waste tray until all cylinders are pumping.

Activate the rotating cone and allow syrup film to flow into the outer shell hopper.

Activate the flavor pumps. Set Menthol-Eucalyptus pump to 31.55 g/min. Set Cherry flavor pump to 50.4 gm/min.

Begin to deposit, both outer shell and center in waste tray. Remove waste tray and begin to deposit into molds.

STEP #6

Check weights and adjust, if necessary, piston lengths of outer shell pistons.

STEP #7

Check weights of center fill lozenge (final weight) and adjust center pistons if necessary.

STEP #8

Allow the deposited lozenges to cool through the cooling funnel.

Collect the lozenges off the cooling belt for packaging.

EXAMPLE 1

The following steps comprise the process for producing an example product, Monarch Adult formula. The example is not intended to limit the invention in any manner whatsoever.

CENTER PREPARATION

STEP 1

Add the following ingredients into a clean 250 liter Skerman mixing tank:

| | |
|---|---|
| (a) Glycerin USP | 151.2 Kg |
| (b) 10% Dextromethorphan Hydrobromide Adsorbate | 76.2 Kg |

Mix using high shear mixing head and scrap surface blade for 30 minute or until a homogeneous mix occurs. When complete mix occurs, apply vacuum for 5 minutes at 22 inches of vacuum. Hold material until Step #4.

STEP #2

Preparation of F D and C RED #40 10% W/W Solution

Add the following to a clean stainless steel container:

| | |
|---|---|
| (a) FD and C Red #40 | 177.3 g |
| (b) Drinking Water | 1.8 Kg |

Mix well and hold with continuous mixing.

STEP #3

Set Autofeed Weigher to weigh the following ingredients:

| | |
|---|---|
| (a) Granulated Sugar | 68.2 Kg |
| (b) Glucose Syrup 63 DE | 85.1 Kg |
| (c) Water | 27.0 Kg |

Transfer material to clean vacuum cooker. Set Autofeed weigher to weigh again the following ingredients:

| | | |
|---|---|---|
| (a) Granulated Sugar | 68.2 | Kg |
| (b) Glucose Syrup 63 DE | 85.1 | Kg |
| (c) Water | 27.0 | Kg |

Transfer material to the vacuum cooker. Add to the vacuum cooker:

| | |
|---|---|
| (d) FD and C Red #40 10% w/w solution | 1950.3 g |

Begin heating to 119° C. at 17 inches of vacuum. Sample syrup for moisture content.

STEP #4

Add to the vacuum cooker containing the cooked syrup the following:

| | |
|---|---|
| (a) 10% Dextromethorphan Hydrobromide adsorbate/ Glycerin Mix | 227.9 Kg |

Mix and flush tank ball valve for 15 minutes. After 15 minutes close vacuum tank cover and begin drawing a vacuum to 22 inches for 5 minutes. Transfer mix to a 450 liter jacketed mixing tank.

STEP #5

Add the following to the syrup made in Step #4 in the 450 liter jacketed mixing tank:

| | |
|---|---|
| (a) l-Methanol | 492.9 g |
| (b) Artifical Cherry Flavor | 4088.2 g |

Mix the syrup slowly for 15 minutes. This syrup is ready for depositing.

STEP #6

Preparation of FD and C Red #40 5% W/W Solution for Outer Shell

Add the following to a clean stainless steel container:

| | |
|---|---|
| (a) FD and C Red #40 Dye | 86.5 g |
| (b) Warm Drinking Water | 2422.5 g |

Mix contents well.

Note: Mix contents before each dispensing.

STEP #7

SET-UP FLAVOR PUMPS

Methanol-Eucalyptus-Menthyl Lactate Artifical Cherry Flavor

Add the following to a clean stainless steel container:

| (a) 1-Methanol USP | 1980.3 g |
|---|---|
| (b) Eucalyptus Oil | 1980.3 g |
| (c) Menthyl Lactate | 1980.3 g |

Mix well and heat to dissolve if needed. Add the mix to the Microfilm Cooker flavor tank. Set pump rate on the flavor pump to 12.7 g/minute.

Add the following to microfilm cooker flavor tank #2.

| (d) Artifical Cherry Flavor | 26,264.4 g |
|---|---|

Set pump rate on the flavor pump #2 to 54.9 g/minute

STEP #8

Set autofeed microprocessor to weigh the following:

| (a) Drinking Water | 27.0 Kg |
|---|---|
| (b) Glucose HM 43DE | 75.0 Kg |
| (c) Granulated Sugar | 75.0 Kg |

Press "ON" for weighing process to begin. Transfer the slurry to J63. Begin to heat the J63 tank to 110° C. At 110° C. transfer the syrup to the syrup reservoir tank #1. Record yield from the load cell of amount of transfer syrup.

STEP #9

Add to reservoir tank #1 the following:

| (a) FD and C Red #40 5% w/w solution | 150 g |
|---|---|
| (b) Benzocaine USP | 395 g |

Mix the syrup until solids dissolve and transfer the syrup to the feed syrup reservoir for the microfilm cooker. Maintain constant agitation in the feed syrup reservoir (Buffer) tank. This syrup is ready for cooking in the microfilm cooker.

STEP #10

Activate power supply on microfilm cooker control panel. Set or record following parameters:

| B and L Pump Setting | 1.8-2.0 |
|---|---|
| Preheater Steam Pressure | 68-70 lb./sq. in. |
| Discharge Pump Pressure | 18-20 lb./sq. in. |
| Microfilm Steam Pressure | 75-85 lb./sq. in. |
| Outlet syrup temperature | 148-150° C. |
| Discharge Pump Setting | 1.0-1.2 |
| Phasing Setting | 48 |
| Outer Shell Volume Setting | 3.4 |
| Center Volume Setting | 2.5 |
| Strokes/Minute Setting | 50 |
| Shell Hopper Temp. Setting | 135° C. |
| Center Hopper Temp. Setting | 50° C. |
| Manifold Temp. Setting | 145° C. |
| Shell Hopper Jacket Simmerstat | 1 |
| Shell Hopper Base Simmerstat | 1 |
| Manifold Heater Simmerstat | 2-4 |
| Center Hopper Simmerstat | 1 or off |
| Center Base Simmerstat | 1 or off |

Discharge the syrup from cooker and adjust the rate to 3500 g/minute. Pump the center syrup made in Step #5 into center hopper. Begin depositing the center syrup in waste tray until all cylinders are pumping. Activate the flavor incorporator and set pump at 25 rpm. Activate flavor pumps. Begin to deposit both outer shell and center in waste tray. Begin to deposit into molds.

STEP #11

Check weights across the molds and record. Adjust if needed to meet target weight.

| Target Weight | 5.63 | Range 5.34 g to 5.91 |
|---|---|---|

EXAMPLE 2

The following steps comprise the process for producing an example product, Monarch Children's Formula. The example is not intended to limit the invention in any manner whatsoever.

CENTER PREPARATION

STEP #1

Add the following ingredients into a clean 250 liter Skerman mixing tank:

| (a) Glycerin USP | 76.1 Kg |
|---|---|
| (b) 10% Dextromethorphan Hydrobromide Adsorbate | 38.6 Kg |

Mix using high shear mixing head and scrap surface blade for 30 minutes or until a homogeneous mix occurs. When complete mix occurs, apply vacuum for 5 minutes at 22 inches of vacuum. Hold material until Step #4.

STEP #2

PREPARATION OF F D AND C RED #40 10% W/W SOLUTION Add the following to a clean stainless steel container:

| (a) FD and C #40 | 89.3 g |
|---|---|
| (b) Drinking Water | 893.0 g |

Mix well and hold with continuous mixing.

STEP #3

Set autofeed weigher to weigh the following ingredients:

| (a) Granulated sugar | 68.7 Kg |
|---|---|
| (b) Glucose syrup 63 DE | 85.7 Kg |
| (c) Water | 27.2 Kg |

Transfer material to a clean vacuum cooker.
Add to the volume cooker:

| (d) FD and C Red #40 10% w/w solution | 982.3 Kg |

Begin heating to 119° C. at 17 inches of vacuum. Sample syrup for moisture content.

STEP #4

Add to the volume cooker containing the cooked syrup the following:

| (a) 10% Dextromethorphan Hydrobromide adsorbate/ Glycerin Mix | 114.8 Kg |

Mix and flush tank ball valve for 15 minutes. After 15 minutes close vacuum tank cover and begin drawing a vacuum to 22 inches for 5 minutes. Transfer mix to a 450 liter jacketed mixing tank.

STEP #5

Add the following to the syrup made in Step #4 in the 450 liter jacketed mixing tank:

| (a) 1-Methanol | 248.4 g |
| (b) Artifical Cherry Flavor | 2059.5 g |

Mix the syrup slowly for 15 minutes. This syrup is ready for depositing.

STEP #6

PREPARATION OF FD AND C RED #40 5% W/W SOLUTION

SOLUTION FOR OUTER SHELL

Add the following to a clean stainless steel container:

| (a) FD and C Red #40 dye | 86.5 g |
| (b) Warm drinking water | 2422.5 g |

Mix contents well.

Note: Mix contents before each dispensing.

STEP #7

SET-UP FLAVOR PUMPS

Methanol—Eucalyptus
Artifical Cherry Flavor
Add the following to a clean stainless steel container:

| (a) 1-Methanol USP | 1309.8 g |
| (b) Eucalyptus Oil | 1309.8 g |

Mix well and heat to dissolve if needed. Add the mix to the microfilm cooker flavor tank. Set pump rate on the flavor pump to 7.0 g/minute.

Add the following to microfilm cooker flavor tank #2.

| (d) Artifical Cherry Flavor | 23,412.0 g |

Set pump rate on the flavor pump #2 to 46.9 g/minute.

STEP #8

Set autofeed microprocessor to weigh the following:

| (a) Drinking Water | 27.0 Kg |
| (b) Glucose HM 43DE | 75.0 Kg |
| (c) Granulated Sugar | 75.0 Kg |

Press "ON" for weighing process to begin. Transfer the slurry to J63. Begin to heat the J63 tank to 110° C. At 110° C. transfer the syrup to the syrup reservoir tank #1. Record yield from the load cell of amount of transfer syrup.

STEP #9

Add to reservoir tank #1 the following:

| (a) FD and C Red #40 w/w solution | 150 g |
| (b) Benzocaine USP | 243 g |

Mix the syrup until solids dissolve and transfer the syrup to the feed syrup reservoir for the microfilm cooker.

Maintain constant agitation in the feed syrup reservoir (Buffer) tank.

This syrup is ready for cooking in the microfilm cooker.

STEP #10

Activate power supply on microfilm cooker control panel. Set or record following parameters:

| B and L Pump Setting | 1.8–2.0 |
| Preheater Steam Pressure | 68–70 lb./sq. in. |
| Discharge Pump Pressure | 18–20 lb./sq. in. |
| Microfilm Steam Pressure | 75–85 lb./sq. in. |
| Outlet syrup temperature | 148–150° C. |
| Discharge Pump Setting | 1.0–1.2 |
| Phasing Setting | 48 |
| Outer Shell Volume Setting | 3.4 |
| Center Volume Setting | 2.5 |
| Strokes/Minute Setting | 50 |
| Shell Hopper Temp. Setting | 135° C. |
| Center Hopper Temp. Setting | 50° C. |
| Manifold Temp. Setting | 145° C. |
| Shell Hopper Jacket Simmerstat | 1 |
| Shell Hopper Base Simmerstat | 1 |
| Manifold Heater Simmerstat | 2–4 |
| Center Hopper Simmerstat | 1 or off |
| Center Base Simmerstat | 1 or off |

Discharge the syrup from cooker and adjust the rate to 2900 g/minute. Pump the center syrup in Step #5 into center hopper. Begin depositing the center syrup in waste tray until all cylinders are pumping. Activate the flavor incorporator and set pump at 25 rpm. Activate flavor pumps. Begin to deposit both outer shell and center in waste tray. Begin to deposit into molds.

STEP #11

Check weights across the molds and record. Adjust if needed to meet target weight.

| | |
|---|---|
| Target weight | 4.17 g |
| Range 3.96 g to 4.37 g | |

The foregoing patents and publications are incorporated herein by reference.

Many variations of this invention will occur to those skilled in this art in light of the above, detailed description. For example, instead of a cough suppressant, the medicament can comprise an antibiotic. Instead of benzocaine, another anesthetic may be used. Instead of dextromethorphan, another cough suppressant can be used. All such obvious variations are within the full intended scope of the appended claims.

I claim:

1. An edible unit dosage form for delivering a medicament selected from the group consisting of menthol, eucalyptus, benzocane, dextramethorphan or a mixture of any of the foregoing comprising:
    (a) an outer relatively hard, unitary shell consisting essentially of a sugar which crystallizes slowly from the melt, said sugar consisting of sucrose, glucose or a mixture thereof; and
    (b) a liquid or semi-solid center core contained within said shell comprising an accurate dose of a medicament, said dose being within about ±5% by weight of the prescribed dosage.

2. An edible unit dosage form for delivering a medicament selected from the group consisting of menthol, eucalyptus, benzooane, dextramethorphan or a mixture of any of the foregoing comprising:
    (a) an outer relatively hard, unitary shell consisting essentially of a sugar which crystallizes slowly from the melt, said sugar consisting of sucrose, glucose, or a mixture thereof; and a flavoring; and
    (b) a liquid or semi-solid center core contained within said shell comprising an accurate dose of a medicament, said dose being within about +5% of the prescribed dosage.

3. An edible unit dosage form for delivering a medicament selected from the group consisting of menthol, eucalyptus, benzocane, dextramethorphan or a mixture of any of the foregoing comprising:
    (a) an outer relatively hard, unitary shell consisting essentially of a sugar consisting of sucrose, glucose or a mixture thereof, a flavoring, and a therapeutic amount of a medicament
    (b) a liquid or semi-solid center core contained within said shell comprising an accurate dose of a medicament, said dose being within about ±5% of the prescribed dosage.

4. An edible unit dosage form as in claim 1 wherein the liquid or semi-solid center core (b) further comprises a sugar syrup.

5. An edible unit dosage form as in claim 1 wherein the medicament liquid or semi-solid center (b) is water soluble.

6. An edible unit dosage form as in claim 3 comprising a cough or cold medicament within the hard outer shell (a) of the dosage form consists of sucrose, glucose, benzocaine, methanol-euclyptus and cherry flavoring; and the liquid or semi-solid center (b) comprises the medicament dextromethorphan and a sugar syrup.

7. A process for preparing an edible unit dosage form for delivering a medicament selected from the group consisting of menthol, eucalyptus, benzocane, dextramethorphan or a mixture of any of the foregoing said process comprising:
    (i) forming a molten shell composition, consisting essentially of a sugar which crystallizes slowly from the melt said sugar consisting of sucrose, glucose or a mixture thereof, simultaneously around a liquid or semi-solid center core composition comprising an acurate dose of a medicament, said dose being within about ±5% by weight of the prescribed dosage; and
    (ii) cooling to solidify and harden said shell composition.

8. The process for preparing the unit dosage form of claim 7 wherein the moisture content of the liquid or semi-solid center is less than or equal to the moisture content of the outer molten shell composition.

9. The process for preparing the unit dosage form of claim 8 wherein the moisture content of the liquid or semi-solid center core composition is less than 5% and is preferably equal to or less than 3%.

10. A process for preparing an edible unit dosage form for delivering a medicament selected from the group consisting of menthol, eucalyptus, benzocane, dextramethorphan or a mixture of any of the foregoing, said process comprising:
    (a) forming a molten shell composition, consisting essentially of a sugar which crystallizes slowly from the melt said sugar consisting of sucrose, glucose or a mixture thereof and a flavoring, simultaneously around a liquid or semi-solid center core composition comprising an accurate dose of a medicament, said dose being within about +5% by weight of the prescribed dosage; and
    (iii) cooling to solidify and harden said shell composition.

11. A process for preparing an edible unit dosage form for delivering a medicament selected from the group consisting of menthol, eucalyptus, benzocane, dextramethorphan or a mixture of any of the foregoing, said process comprising:
    (a) forming a molten shell composition, consisting essentially of a sugar which crystallizes slowly from the melt said sugar consisting of sucrose, glucose or a mixture thereof a flavoring and a therapeutic amount of medicament, simultaneously around a liquid or semi-solid center core composition comprising an accurate dose of a medicament, said dose being within about +5% by weight of the prescribed dosage; and
    (iii) cooling to solidify and harden said shell composition.

12. The process for preparing the unit dosage form of claim 11 wherein said medicament is selected from menthol, eucalyptus, benzocaine or a mixture of any of the foregoing.

13. The process for preparing the unit dosage form of claim 7 wherein the molten shell composition is water soluble.

14. The process for preparing the unit dosage form of claim 7 wherein the liquid or semi-solid center core com-position further comprises a sugar syrup.

15. The process for preparing the unit dosage form of claim 7 wherein the liquid or semi-solid center core com-position is water soluble.

16. The process for preparing the unit dosage of claim 8 wherein the moisture content of the liquid or semi-solid center core is lowered to that of, or less than that of the moisture content of the molten shell composition by the use of heat and vacuum.

* * * * *